United States Patent [19]

Tao

[11] 4,394,510
[45] Jul. 19, 1983

[54] PROCESS FOR PREPARING AN ISOXAZOLYLUREA

[75] Inventor: Eddie V. P. Tao, Indianapolis, Ind.

[73] Assignee: Eli Lilly and Company, Indianapolis, Ind.

[21] Appl. No.: 230,555

[22] Filed: Feb. 2, 1981

[51] Int. Cl.$^3$ ............................................. C07D 261/14
[52] U.S. Cl. ..................................... 548/240; 548/246; 548/241
[58] Field of Search .......................... 548/240, 246, 241

[56] References Cited

U.S. PATENT DOCUMENTS

| | | | |
|---|---|---|---|
| 4,028,376 | 6/1977 | Yukinaga et al. | 260/307 H |
| 4,062,861 | 12/1977 | Yukinaga et al. | 260/307 H |
| 4,200,757 | 4/1980 | Makisumi et al. | 548/246 |
| 4,256,899 | 3/1981 | Makisumi et al. | 548/246 |
| 4,259,501 | 3/1981 | Burow et al. | 548/246 |

FOREIGN PATENT DOCUMENTS

| | | | |
|---|---|---|---|
| 10262 | 4/1980 | European Pat. Off. | 548/246 |
| 2825194 | 12/1978 | Fed. Rep. of Germany | 548/246 |
| 48-42062 | 12/1973 | Japan | 260/453 PH |
| 51-63170 | 6/1976 | Japan | 548/240 |
| 51-75064 | 7/1976 | Japan | 548/246 |

OTHER PUBLICATIONS

Technical Report on EL-187, Research Report Prepared by Lilly Research Laboratories.

*Primary Examiner*—Donald G. Daus
*Assistant Examiner*—G. Hendricks
*Attorney, Agent, or Firm*—Joseph A. Jones; Arthur R. Whale

[57] ABSTRACT

The herbicide 1-(5-t-butylisoxazol-3-yl)-3,3-dimethylurea is prepared in high yield and high purity by a multiple-step process without the isolation of intermediate products.

12 Claims, No Drawings

PROCESS FOR PREPARING AN ISOXAZOLYLUREA

BACKGROUND OF THE INVENTION

1. Field of the Invention

This invention belongs to the field of agricultural chemistry, and provides a particularly advantageous process for preparing 1-(5-t-butylisoxazol-3-yl)-3,3-dimethylurea, a known herbicide.

2. State of the Art

The compound prepared by the process of this invention is patented by Shionogi and Company, U.S. Pat. No. 4,062,861. The compound is under development as a commercial herbicide, and is the subject of a technical data sheet entitled Technical Report on EL-187, published by Eli Lilly and Company, Indianapolis, Ind., United States.

SUMMARY OF THE INVENTION

This invention provides a process for preparing 1-(5-t-butylisoxazol-3-yl)-3,3-dimethylurea comprising 1. combining a $C_1$-$C_6$ alkyl pivalate with acetonitrile in the presence of sodium hydride, potassium t-butoxide or sodamide at from about 80° to about 110°, extracting the reaction mixture with water, acidifying the water layer, extracting the acidic water layer with an inert organic solvent, and extracting the organic layer with aqueous sodium hydroxide;

2. combining the basic aqueous layer with hydroxylamine or a salt thereof, adjusting the pH of the mixture to from about 7.5 to about 8.5, and holding the mixture at from about 70° to about 100°, combining the mixture with from about 0.5 to about 2 moles of concentrated hydrochloric acid per mole of pivalate, holding the mixture at from about 50° to about 100°, combining the mixture with from about 1 to about 3 moles of concentrated hydrochloric acid per mole of pivalate, holding the mixture at from about 50° to about 100°, cooling the mixture, extracting the mixture with cyclohexane, making the aqueous layer basic with sodium hydroxide, cooling the basic mixture, extracting the mixture with ethyl acetate, and drying the organic layer;

3. slowly adding the dried organic layer to a solution of phosgene in ethyl acetate at from about −25° to about 5°, holding the mixture at from about 60° to about 100°, and cooling the mixture;

4. combining the cooled mixture with dimethylamine, holding the mixture at from about 60° to about 100°, cooling the mixture, neutralizing the mixture with aqueous acid, concentrating the organic layer to a volume of from about 180 to about 300 ml. per gram-mole of pivalate, adding the hot concentrated solution to water, cooling the mixture to from about 0° to about 10°, and separating the solid product.

DESCRIPTION OF THE PREFERRED EMBODIMENTS

In the above statement of the invention, all temperatures are stated in degrees Celsius. The term $C_1$-$C_6$ alkyl pivalate includes compounds such as methyl, ethyl, isopropyl, isopentyl, isobutyl, hexyl, and 3-methylbutyl pivalates.

The process of this invention is particularly advantageous because it is capable of preparing the valuable herbicide which is its product in high overall yields, and without isolation of intermediate products. Process chemists will observe that all of the intermediate products are obtained as solutions, and that all of the purification steps are simple extractions which may be carried out in large-volume closed equipment by merely stirring and separating layers. Thus, the process is quite appropriate for large-scale production of the isoxazolylurea. It will also be observed that the starting compounds are inexpensive, and that the various solvents and reagents are inexpensive and free of excessive fire or toxicity hazards.

In general, no substantial excess amounts of reagents are used in this process. Unless otherwise specifically discussed below, approximately stoichiometric amounts of all reagents are used. Of course, as is usual in organic chemistry, small excess amounts of the less expensive reagents may be advantageously used to assure that the more expensive reagents are fully consumed. For this purpose, small excess amounts in the range of about 5-25% are appropriate. Larger excess amounts are not harmful and may be used if desired in special circumstances.

No particularly intensive mixing is necessary in any step of this process. The reaction mixtures are of moderate viscosity at the operating temperatures, and ordinary mixing equipment appropriate for agitating solutions and light suspensions is adequate in all steps.

The process includes a number of extraction steps. These steps are carried out in the ordinary manner, by mixing the two phases for a period of time adequate to insure good contact in the mixing equipment in use, and allowing the layers to separate. The preferred solvents and operating conditions are chosen so as to avoid any serious emulsion problems in separating the layers.

The various extraction steps may be carried out in a single stage, or may be carried out by adding multiple portions of one phase to the other phase and repeatedly separating the layers, as may be more efficient and economical in a given instance. It is necessary, of course, to balance the improvement in efficiency of the extraction by using multiple portions of the extracting phase, against the increased operator time and effort necessary.

The concentration of the reaction mixtures is not critical, except at the final isolation step as described at the end of the description of step 4. In general, it is convenient to operate at a concentration of 1.5 liters per gram-mole in step 1, and at a concentration of 1 liter per gram-mole in the other steps. The range of practical concentrations depends in part on the power of the mixing equipment in use, and in part on the chosen solvents. The preferred concentrations just given are high enough to be quite economical and convenient in large-scale production, however, and there is little benefit in operating at higher concentrations. Lower concentrations may of course be used, and may even be necessary, if for example, a particular weak solvent must be used for reasons of economy. It will be understood, of course, that it will not be possible to carry out the desired smooth transfer of the intermediate products from step to step if an intermediate product is allowed partially to precipitate.

It has not been found necessary to perform any high-efficiency purification steps, such as activated charcoal treatment, in the course of the various steps of this process. It is advisable, however, to filter the intermediate product-containing solutions from time to time as they are transferred between vessels. No exceptionally effective filtration techniques are necessary; ordinary filter paper and filter-aid pads are adequate. All of the solutions are free-filtering and essentially clear; filtration is advisable from time to time, however, to assure that impurities in the reagents are not carried too far through intermediate steps.

The intermediate compounds which are prepared in the course of the process are not isolated, and in normal operation of the process no in-process analysis or identification of the intermediates is necessary. It should be observed, however, that the intermediate product of the first step is 2,2,2-trimethylacetylacetonitrile; the product of the second step is 3-amino-5-t-butylisoxazole; and the product of the third step is a mixture of 5-t-butyl-3-isocyanatoisoxazole and N-(5-t-butylisoxazol-3-yl)carbamoyl chloride.

The individual steps will be discussed in detail.

STEP 1

In this step, a $C_1$-$C_6$ alkyl pivalate is reacted with acetonitrile to prepare the corresponding ketonitrile. Any such alkyl pivalate may be used, but it has been found that isobutyl pivalate is a preferred starting compound. The reaction is carried out in an inert organic solvent, of which cyclohexane, benzene, toluene and the xylenes are preferred solvents.

The reaction is carried out in the presence of a strong base chosen from sodium hydride, potassium t-butoxide and sodamide. It is advisable to use more than a molar quantity of the strong base; 2 moles of strong base per mole of alkyl pivalate is a preferred amount, although amounts of strong base from about 1 mole per mole of pivalate upwards are satisfactory; ordinarily it is unnecessary to use an amount of base greater than about 3 or 4 moles per mole of alkyl pivalate.

It is preferable to carry the reaction out by combining the pivalate and the acetonitrile, and adding the solution slowly to a solution or dispersion of the strong base.

The reaction is carried out at a temperature from about 80° to about 110°. As usual, it is most convenient to choose a solvent which will give a reaction mixture which has the desired reflux temperature at the desired operating pressure. Cyclohexane is particularly convenient in this regard. A preferred reaction time, when the solvent is cyclohexane and the reaction is at the reflux temperature, is about 8 hours.

When the reaction is as complete as is desired, the reaction mixture is cooled and extracted with water. It will be understood that the first portions of water should be added quite slowly to avoid explosive decomposition of the strong base. The water layer, which contains the intermediate product as a salt, may be extracted with an organic solvent such as toluene, if the strong base was sodium hydride in a mineral oil suspension, and if the reaction solvent was one, such as cyclohexane, which does not have a high affinity for the mineral oil.

The water layer is made acid with any convenient water-soluble acid, preferably an inexpensive mineral acid such as hydrochloric acid, and is then extracted with a convenient inert organic solvent. Toluene is a particularly convenient solvent at this point, but the extraction may be carried out with any appropriate water-immiscible organic solvent, such as benzene or a xylene. Finally, the organic layer from the extraction is extracted with an aqueous solution of sodium hydroxide, to re-convert the intermediate ketonitrile to the sodium salt, and to transfer it to the water layer.

STEP 2

In this step, the basic aqueous layer from step 1 is combined with hydroxylamine or a salt thereof to cyclize the ketonitrile and form the isoxazole. It is preferred to use the hemisulfate salt of hydroxylamine, but other salts are equally appropriate as may be convenient in a given instance. For example, the hydrochloride, phosphate, nitrate, acetate, methanesulfonate and toluenesulfonate salts of hydroxylamine, or the free amine itself, are quite appropriate.

The pH of the aqueous reaction mixture is then adjusted to a value from about 7.5 to about 8.5. Some care in the pH adjustment is advisable, because it has been found that the pH has a strong influence on the yield of this step. When the hemisulfate salt of hydroxylamine is used, it is most advantageous to adjust the pH to from 8.35 to 8.45. The mixture is then heated to a temperature in the range of from about 70° to about 100°, and is stirred at that temperature for a time, preferably for about 4 hours.

The reaction mixture is treated twice with hydrochloric acid to form the desired isoxazole and to remove a byproduct. To the mixture is first added from about 0.5 to about 2 moles of concentrated hydrochloric acid per mole of starting pivalate, preferably about 1 mole, and the mixture is stirred at from about 50° to about 100°, preferably about 70°, for a short time, preferably about 30 minutes. A second portion of concentrated hydrochloric acid, from about 1 to about 3 moles per mole of starting pivalate, preferably about 1.5 moles, is then added, and the mixture is stirred at from about 50° to about 100°, preferably at about the reflux temperature, for a short time, preferably about 0.5 to 1 hour.

The reaction mixture is then cooled to approximately ambient temperature, and is extracted with cyclohexane to remove the remaining by-product. The layers are separated, and the product-containing aqueous layer is made basic with sodium hydroxide.

The basic mixture is again cooled to ambient temperature, and is extracted with ethyl acetate. The organic layer is then dried to remove water, as by passing it through a layer of 3 A or 4 A molecular sieves, or over a pad of a desiccating salt such as magnesium sulfate, or by azeotropic distillation.

STEP 3

The dried organic layer obtained from step 2 is slowly added with stirring to a cold solution of phosgene in ethyl acetate, while the temperature of the stirred mixture is held at from about −25° to about 5°, preferably at from about −15° to about 0°. The length of time spent on the addition depends, of course, on the intensity of the mixing device, and upon the scale of the operation. For example, on 0.5 gram-mole scale, the addition is preferably carried out over a period of about 30 minutes. In large-scale equipment, the addition might appropriately take in the range of 1–4 hours. It is necessary to keep the temperature in the stated range, and to perform the addition slowly enough that the mixture is constantly homogeneous and locally high concentrations of the isoxazole solution do not occur. After the addition is complete, the mixture is heated to a temperature from about 60° to about 100°, preferably to the reflux temperature of the mixture, and is held at that temperature for a short time, preferably for about 1.5 hours. The reaction mixture is then cooled to about ambient temperature.

STEP 4

The reaction mixture from step 3 is combined with dimethylamine, and the mixture is heated to a temperature from about 60° to about 100°, preferably to the reflux temperature, and is stirred at that temperature for a brief time, preferably for about 2 hours. The reaction mixture is then cooled to about ambient temperature, and is neutralized with aqueous acid. Any appropriate water-soluble acid may be used, preferably hydrochloric acid; other convenient acids such as sulfuric acid, acetic acid, nitric acid and the like may also be used as convenient. The acid is needed to neutralize residual dimethylamine, and to remove the resulting dimethylamine salt and water from the reaction mixture; accordingly, an aqueous acid is needed so that it will be possible to separate the layers. After the layers have been separated, the organic layer, containing the desired product, is concentrated by evaporation or distillation to a volume from about 180 ml. to about 300 ml. per gram-mole of starting pivalate. The preferred volume is from about 180 to about 250 ml. per gram-mole. The adjustment of concentration is needed, because the precipitation of the final product is adversely affected by excessive solvent in the product solution.

Finally, the product isoxazolylurea is isolated by pouring the hot product-containing solution into a large amount of water, cooling the aqueous mixture to a temperature from about 0° to about 10°, and separating the precipitated product, as by filtration or centrifugation.

It has been found that the product obtained by this process is extremely pure as it comes from the precipitation and filtration, with no final treatment except drying.

A preferred embodiment of this invention is the portion of the process as a whole which comprises preparing the isoxazolylurea from 3-amino-5-t-butylisoxazole, which process comprises slowly adding an ethyl acetate solution of 3-amino-5-t-butylisoxazole to a solution of phosgene in ethyl acetate at from about −25° to about 5°, holding the mixture at from about 60° to about 100°, and cooling the mixture; combining the cooled mixture with dimethylamine, holding the mixture at from about 60° to about 100°, cooling the mixture, neutralizing the mixture with aqueous acid, concentrating the organic layer to a volume of from about 300 to about 500 ml. per gram-mole of isoxazole, preferably from about 300 to about 400 ml., adding the hot concentrated solution to water, cooling the mixture to from about 0° to about 10°, and separating the solid product. The preferred conditions for this embodiment are as described above in the detailed discussion of steps 3 and 4.

The following examples further illustrate the invention.

PREPARATION 1

A 51 g. portion of pivalic acid, 37 g. of isobutyl alcohol, 100 ml. of cyclohexane and 1.3 g. of concentrated sulfuric acid were combined and stirred at the reflux temperature for 5 hours, while water was removed from the condensate in a trap. The mixture was then cooled to 30°, and was washed successively with two 100 ml. portions of water, two 25 ml. portions of saturated aqueous sodium bicarbonate, and two 50 ml. portions of water. The reaction mixture was then heated to reflux and dried azeotropically, and cooled for use in Example 1. The solution contained 0.5 gram-mole of isobutyl pivalate.

EXAMPLE 1

A 26.4 g. portion of sodium hydride, as a mineral oil dispersion, was added to 640 ml. of cyclohexane, and the mixture was heated to reflux. To the product solution from Preparation 1 was added 28.7 g. of acetonitrile, and the solution was added dropwise with stirring to the refluxing sodium hydride suspension. After the addition was complete, the mixture was stirred under reflux for seven hours, and cooled to ambient temperature.

To it was added 500 ml. of water (the first 100 ml. was added very slowly with cooling) at 40°. The layers were separated, and the aqueous layer was filtered through a filter aid pad. The filtered aqueous mixture was extracted with 100 ml. of toluene, and was acidified by the addition of 128 ml. of concentrated hydrochloric acid, with cooling. The acidic mixture was then extracted with 300 ml. of toluene, and then with 200 ml. of toluene. The organic layers were combined and washed with 100 ml. of saturated aqueous sodium bicarbonate. The 2-phase mixture was filtered through a filter aid pad and the layers were separated. To the organic layer was added 37 g. of 50% aqueous sodium hydroxide and 240 ml. of water.

The layers were separated, and the aqueous layer was mixed with a solution of 36.2 g. of hydroxylamine hemisulfate in 160 ml. of water. The mixture was then heated to 70°, and stirred at that temperature for 4 hours. To the mixture was added 44 ml. of concentrated hydrochloric acid, and the mixture was stirred at 70° for 30 minutes. To it was added 67 ml. of additional concentrated hydrochloric acid, and the mixture was stirred under reflux for 40 minutes.

The mixture was then cooled to ambient temperature, and extracted with 125 ml. of cyclohexane. The layers were separated, and the organic layer was back-extracted with 10 ml. of concentrated hydrochloric acid in 100 ml. of water. The aqueous layers were combined, and to the aqueous solution was added 80 ml. of 50% aqueous sodium hydroxide, with cooling to maintain the temperature at 25°-35°. The solution was then extracted twice with 300 ml. portions of ethyl acetate, and the combined organic layers were washed with 150 ml. of brine. The organic layer was then dried over magnesium sulfate.

The mixture was filtered to remove the magnesium sulfate, and the filter was washed with 100 ml. of dry ethyl acetate. The volume of the solution was reduced by 450 ml. by distillation, and the solution was cooled to ambient temperature. It was added to a solution of 27 ml. of phosgene in 150 ml. of ethyl acetate at −15° over a period of 35 minutes, and was then allowed to warm slowly to ambient temperature.

The mixture was then heated to the reflux temperature, and was stirred at that temperature for 90 minutes. It was then cooled to 25°, and mixed with 36 ml. of dimethylamine. The mixture was heated to reflux, stirred at that temperature for two hours, cooled to ambient temperature, and neutralized by the addition of 24 ml. of 1 N hydrochloric acid. The layers were separated, and the aqueous layer was back-extracted with 75 ml. of ethyl acetate. The organic layers were combined, and 385 ml. of ethyl acetate was removed by distillation. The hot organic solution, near its boiling point, was added to 700 ml. of water.

The 2-phase mixture was chilled to 5° and filtered, and the solids were washed with 200 ml. of water and vacuum dried to obtain 66.2 g. of 1-(5-t-butylisoxazol-3-yl)-3,3-dimethylurea, hemihydrate, which was found to be 95.5% pure by high-pressure liquid chromatography. The yield was 57.5% of the theoretical yield, calculating from the pivalic acid and isobutyl alcohol used in Preparation 1.

EXAMPLE 2

A 14.6 g. portion of 3-amino-5-t-butylisoxazole dissolved in 90 ml. of ethyl acetate was added at −15° to 9 ml. of phosgene dissolved in 25 ml. of ethyl acetate over a period of 10 minutes. The mixture was allowed to warm slowly to ambient temperature, and was then heated to reflux and stirred under reflux for 90 minutes. Twenty-five ml. of solvent was removed by distillation, and 12 ml. of dimethylamine was added and the mixture was stirred under reflux for 1 hour. Sixty ml. of solvent was distilled off, and the remaining hot mixture was added to 100 ml. of water containing 2.2 g. of concentrated hydrochloric acid. The mixture was then chilled to 5° and filtered, and the solids were washed with two 50 ml. portions of water. The product was dried under vacuum at 35° to obtain 22.1 g. of dried product which analyzed 98.8% by high pressure liquid chromatography, corresponding to a corrected yield of 99.3%.

EXAMPLE 3

The process was carried out according to the process of Example 2, except that the phosgene-isoxazole mixture was heated immediately to the reflux temperature as soon as the addition was complete, and was stirred under reflux for 2 hours, and, after the dimethylamine had been added, the mixture was stirred for 2 hours, instead of 1 hour as in Example 2. The yield was 20.8 g. of product which analyzed 98.5%, corresponding to a yield of 93.2% of the theoretical yield.

EXAMPLE 4

To 135 liters of ethyl acetate in a stainless steel tank was added 28.56 kg. of 3-amino-5-t-butylisoxazole, as a wet filter cake containing 22.4 kg. of pure compound. The isoxazole was dissolved with stirring, and the solution was added to a solution of 23.6 kg. of phosgene in 150 liters of ethyl acetate at −5° to 0° in a glass-lined tank. The addition was made over a period of 1 hour 50 minutes, holding the temperature of the glass-lined tank constant. The first tank and hoses were washed with 20 liters of ethyl acetate, and the mixture was warmed to the ambient temperature over a period of 30 minutes, and was then heated to the reflux temperature over a period of thirty minutes more. The mixture was then stirred under reflux for 90 minutes, at about 73°. The mixture was then cooled to ambient temperature, and nitrogen was bubbled through it to sweep out gasses.

To the mixture was then added 12.6 kg. of dimethylamine, and the mixture was then heated and stirred for 90 minutes under reflux, at a temperature of 79°. The mixture was then cooled to ambient temperature, and to it was added 25 liters of 1 N hydrochloric acid and 50 liters of deionized water, and the mixture was agitated, and the layers were allowed to separate. The aqueous layer was removed and discarded. The mixture was then distilled and about 245 liters of solvent was removed under vacuum. The remaining contents of the still was added quickly, with agitation, to 320 liters of deionized water in a stainless steel tank. The addition was complete in 5 minutes, and the tank and lines were rinsed with 15 liters of ethyl acetate.

The aqueous mixture was then cooled to 0°–5°, with moderate agitation, and was filtered on a vacuum filter, and the tank was rinsed with additional clean water. The filter cake was washed twice with 70-liter portions of deionized water, and the product was dried under vacuum at 35°. The yield was 31.1 kg. of the desired product.

I claim:

1. A process for preparing 1-(5-t-butylisoxazol-3-yl)-3,3-dimethylurea without isolation of intermediates, consisting essentially of
    (1) combining a $C_1$–$C_6$ alkyl pivalate with acetonitrile in the presence of sodium hydride, potassium t-butoxide or sodamide at from about 80° to about 110°, extracting the reaction mixture with water, acidifying the water layer, extracting the acidic water layer with an inert organic solvent, and extracting the organic layer with aqueous sodium hydroxide;
    (2) combining the basic aqueous layer with hydroxylamine or a salt thereof, adjusting the pH of the mixture to from about 7.5 to about 8.5, and holding the mixture at from about 70° to about 100°, combining the mixture with from about 0.5 to about 2 moles of concentrated hydrochloric acid per mole of pivalate, holding the mixture at from about 50° to about 100°, combining the mixture with from about 1 to about 3 moles of concentrated hydrochloric acid per mole of pivalate, holding the mixture at from about 50° to about 100°, cooling the mixture, extracting the mixture with cyclohexane, making the aqueous layer basic with sodium hydroxide, cooling the basic mixture, extracting the mixture with ethyl acetate, and drying the organic layer;
    (3) slowly adding the dried organic layer to a solution of phosgene in ethyl acetate at from about −25° to about 5°, holding the mixture at from about 60° to about 100°, and cooling the mixture;
    (4) combining the cooled mixture with dimethylamine, holding the mixture at from about 60° to about 100°, cooling the mixture, neutralizing the mixture with aqueous acid, concentrating the organic layer to a volume of from about 180 to about 300 ml. per gram-mole of pivalate, adding the hot concentrated solution to water, cooling the mixture to from about 0° to about 10°, and separating the solid product.

2. A process of claim 1 wherein the alkyl pivalate is combined with acetonitrile in cyclohexane.

3. A process of either of claims 1 or 2 wherein sodium hydride is present.

4. A process of claim 1 wherein, in step 2, the hydroxylamine is in the form of the hemi-sulfate salt.

5. A process of claim 1 wherein, in step 3, the mixture is held at about its reflux temperature.

6. A process of claim 1 wherein, in step 4, the mixture is held at about its reflux temperature.

7. A process of either of claims 1 or 6 wherein, in step 4, the organic layer is concentrated to a volume of from about 180 to about 250 ml. per gram-mole of pivalate.

8. A process for preparing 1-(5-t-butylisoxazol-3-yl)-3,3-dimethylurea comprising slowly adding an ethyl acetate solution of 3-amino-5-t-butylisoxazole to a solution of phosgene in ethyl acetate at from about −25° to about 5°, holding the mixture at from about 60° to about 100°, and cooling the mixture; combining the cooled mixture with dimethylamine, holding the mixture at from about 60° to about 100°, cooling the mixture, neutralizing the mixture with aqueous acid, concentrating the organic layer to a volume of from about 300 to about 500 ml. per gram-mole of isoxazole, adding the hot concentrated solution to water, cooling the mixture to from about 0° to about 10°, and separating the solid product.

9. A process of claim 8 wherein the mixture of the isoxazole and phosgene is held at about its reflux temperature.

10. A process of either of claims 8 or 9 wherein, after the cooled mixture is combined with dimethylamine, the mixture is held at about its reflux temperature.

11. The process of either of claims 8 or 9 wherein the organic layer is concentrated to a volume of from about 300 to about 400 ml. per gram-mole of isoxazole.

12. A process of claim 10 wherein the organic layer is concentrated to a volume of from about 300 to about 400 ml. per gram-mole of isoxazole.

* * * * *